(12) United States Patent
Guzman

(10) Patent No.: US 11,523,855 B2
(45) Date of Patent: Dec. 13, 2022

(54) SPINAL PAIN MANAGEMENT SYSTEM AND METHOD

(71) Applicant: Team Neuro LLC, Fortville, IN (US)

(72) Inventor: Michael F. Guzman, Fortville, IN (US)

(73) Assignee: Team Neuro LLC, Fortville, IN (US)

( * ) Notice: Subject to any disclaimer, the term of this patent is extended or adjusted under 35 U.S.C. 154(b) by 890 days.

(21) Appl. No.: 16/404,845

(22) Filed: May 7, 2019

(65) Prior Publication Data
US 2020/0100828 A1    Apr. 2, 2020

Related U.S. Application Data

(60) Provisional application No. 62/745,723, filed on Oct. 15, 2018, provisional application No. 62/737,956, filed on Sep. 28, 2018.

(51) Int. Cl.
| | | |
|---|---|---|
| *A61B 18/02* | (2006.01) | |
| *A61B 5/15* | (2006.01) | |
| *A61F 7/02* | (2006.01) | |

(52) U.S. Cl.
CPC ........ *A61B 18/02* (2013.01); *A61B 5/150129* (2013.01); *A61B 2018/0212* (2013.01); *A61B 2018/0293* (2013.01); *A61F 2007/0285* (2013.01)

(58) Field of Classification Search
CPC ............................ A61B 18/02; A61B 18/0218
See application file for complete search history.

(56) References Cited

U.S. PATENT DOCUMENTS

| | | | |
|---|---|---|---|
| 7,713,266 B2 | 5/2010 | Elkins et al. | |
| 7,850,683 B2 | 12/2010 | Elkins et al. | |
| 7,862,558 B2 | 1/2011 | Elkins et al. | |
| 7,998,137 B2 | 8/2011 | Elkins et al. | |
| 8,298,216 B2* | 10/2012 | Burger | ............... A61B 18/0218 606/22 |
| 8,409,185 B2 | 4/2013 | Burger et al. | |
| D683,733 S | 6/2013 | Mendoza et al. | |
| D702,848 S | 4/2014 | Mendoza et al. | |
| 8,715,275 B2 | 5/2014 | Burger et al. | |
| 9,101,346 B2 | 8/2015 | Burger et al. | |
| 9,907,693 B2 | 3/2018 | Burger et al. | |
| 2002/0095144 A1* | 7/2002 | Carl | ....................... A61B 18/02 607/113 |

* cited by examiner

*Primary Examiner* — Kaitlyn E Smith
(74) *Attorney, Agent, or Firm* — Woodard Emhardt Henry Reeves & Wagner LLP

(57) ABSTRACT

A method for anesthetizing a human patient undergoing surgery and/or pain block procedure, the method comprising sterilizing the patient's skin including a target region, the target region including a surgical site including the patient's spine; inserting at least one cryo-needle into a first tissue region, the cryo-needle having a distal end configured to cool surrounding patient tissue, the first tissue region comprising soft tissue superficial to the one or more vertebra and on a first lateral side of the patients spine; cooling the distal end of the cryo-needle to cause cooling of surrounding patient tissue thus inhibiting one or more sensory nerves in the surrounding patient tissue; thereafter, performing spinal surgery on the patient's spine at the surgical site; and, thereafter, performing an erector spinae plane block to further inhibit nerves post-operatively in the target region.

13 Claims, 5 Drawing Sheets

SPINAL PAIN MANAGEMENT SYSTEM AND METHOD

CROSS-REFERENCE TO RELATED APPLICATIONS

This application claims the benefit of U.S. Provisional Application No. 62/737,956, filed Sep. 28, 2018, and U.S. Provisional Application No. 62/745,723, filed Oct. 15, 2018, both of which are hereby incorporated by reference.

BACKGROUND

The present invention relates to pain reduction associated with spinal nerves for the human body.

Surgery can involve any area of the body. Anterior, lateral, and posterior areas of the body receive innervation from the spinal cord. This invention relates to targeted blockade of nerve impulses immediately after leaving the spinal canal. Potential target areas include cervical, thoracic, lumbar, and sacral spine. Etiology for surgery can include congenital, idiopathic, traumatic, or more common are related to wear and tear from aging. Patients are typically discharged with opiates, thus creating a potential cycle for chronic opiate consumption. The present invention relates to pain control alternatives for blocking nerves exiting the spine and may be an alternative which will reduce opiate consumption after routine and complex surgery. The invention may allow some patients to avoid surgery.

SUMMARY

The claims, and only the claims, recite the invention. In summary, it may include methods for treating a patient, more particularly methods for anesthetizing a human patient undergoing anterior, posterior, lateral, and/or spinal surgery and/or pain block procedures. The method comprising: sterilizing the patient's skin including a target region, the target region including a surgical site including the patient's spine; inserting at least one cryo-needle into a first tissue region, the cryo-needle having a distal end configured to cool surrounding patient tissue, the first tissue region comprising soft tissue superficial to the one or more vertebra and on a first lateral side of the patients spine; cooling the distal end of the cryo-needle to cause cooling of surrounding patient tissue thus inhibiting one or more sensory nerves in the surrounding patient tissue; thereafter, performing spinal surgery on the patient's spine at the surgical site; and, thereafter, performing an erector spinae plane block to further inhibit nerves post-operatively in the target region. In some forms the spinal surgery comprises at least one of: a spinal fusion, a discectomy, a laminectomy, and/or a pain block. In certain embodiments, the one or more inhibited nerves includes nerves of the dorsal ramus. In some forms the surgery comprises one or more anterior, posterior, and/or lateral body procedures which are innervated by spinal nerves, for example one or more spinal nerves extending from C5 to the sacral nerves.

In certain embodiments, the erector spinae plane block is performed with a local anesthesia. In some forms the local anesthesia is delivered using an imageable needle.

In certain embodiments the erector spinae plane block is performed using an elongate cryo-needle. In some forms the elongate cryoneedle is imageable.

In certain embodiments the cryo-needle comprises two or more needle ends configured to cool surrounding patient tissue. In some forms the two or more needle ends are configured in a generally linear array.

In certain embodiments the method further comprises inserting at least one cryo-needle into a second patient tissue region, the cryo-needle having a distal end configured to cool surrounding patient tissue, the second patient tissue region comprising soft tissue superficial to the one or more vertebra and on a second lateral side of the patients spine opposing said first tissue region.

In certain embodiments the inserting and cooling steps are repeated along a portion of the patients spinal column. In some forms the inserting and cooling steps are repeated in such a way so that progressing in a cranial or caudal direction each subsequent target region is laterally offset from the prior target region.

In certain embodiments the present disclosure provides a method for anesthetizing a patient, the method comprising: inserting at least one cryo-needle into a first tissue region, the cryo-needle having a distal end configured to cool surrounding patient tissue, the first tissue region comprising soft tissue superficial to one or more vertebra and on a first lateral side of the patients spine; cooling the distal end of the cryo-needle to cause cooling of surrounding patient tissue at the first tissue region thus inhibiting one or more sensory nerves in the surrounding tissue; inserting at least one cryo-needle into a second tissue region, the cryo-needle having a distal end configured to cool surrounding patient tissue, the second tissue region comprising soft tissue superficial to one or more vertebra and on the first lateral side of the patient's spine; and cooling the distal end of the cryo-needle to cause cooling of surrounding patient tissue at the second tissue region thus inhibiting one or more sensory nerves in the surrounding tissue.

In certain embodiments the above method also comprises inserting at least one cryo-needle into a third tissue region, the cryo-needle having a distal end configured to cool surrounding patient tissue, the third tissue region comprising soft tissue superficial to one or more vertebra and on the first lateral side of the patient's spine; and cooling the distal end of the cryo-needle to cause cooling of surrounding patient tissue at the third tissue region thus inhibiting one or more nerves in the surrounding tissue.

In certain embodiments the cryo-needle comprises two or more needle ends configured to cool surrounding patient tissue. In some forms the two or more needle ends are configured in a generally linear array.

In certain embodiments the inserting and cooling steps are repeated along a portion of the patient's spinal column. In some forms the inserting and cooling steps are repeated in such a way so that progressing in a cranial or caudal direction each subsequent tissue region is laterally offset from the prior target region.

In certain embodiments the inserting and cooling steps are repeated on the second lateral side of the patient's spine.

In certain embodiments the method further comprising performing a pain block or spinal surgery involves spinal nerve distribution from one or more spinal nerves extending from the cervical spine to sacrum with innervation of anterior, lateral, and/or posterior of a patient's spine. In some forms the spinal surgery comprises at least one of: a spinal fusion, a discectomy, and/or a laminectomy.

In certain embodiments the one or more inhibited nerves includes nerves of the dorsal ramus.

In certain embodiments, both the erector spinae needle and cryoneurolysis needles may be insulated, thus allowing electrical stimulation and evaluation of motor function.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
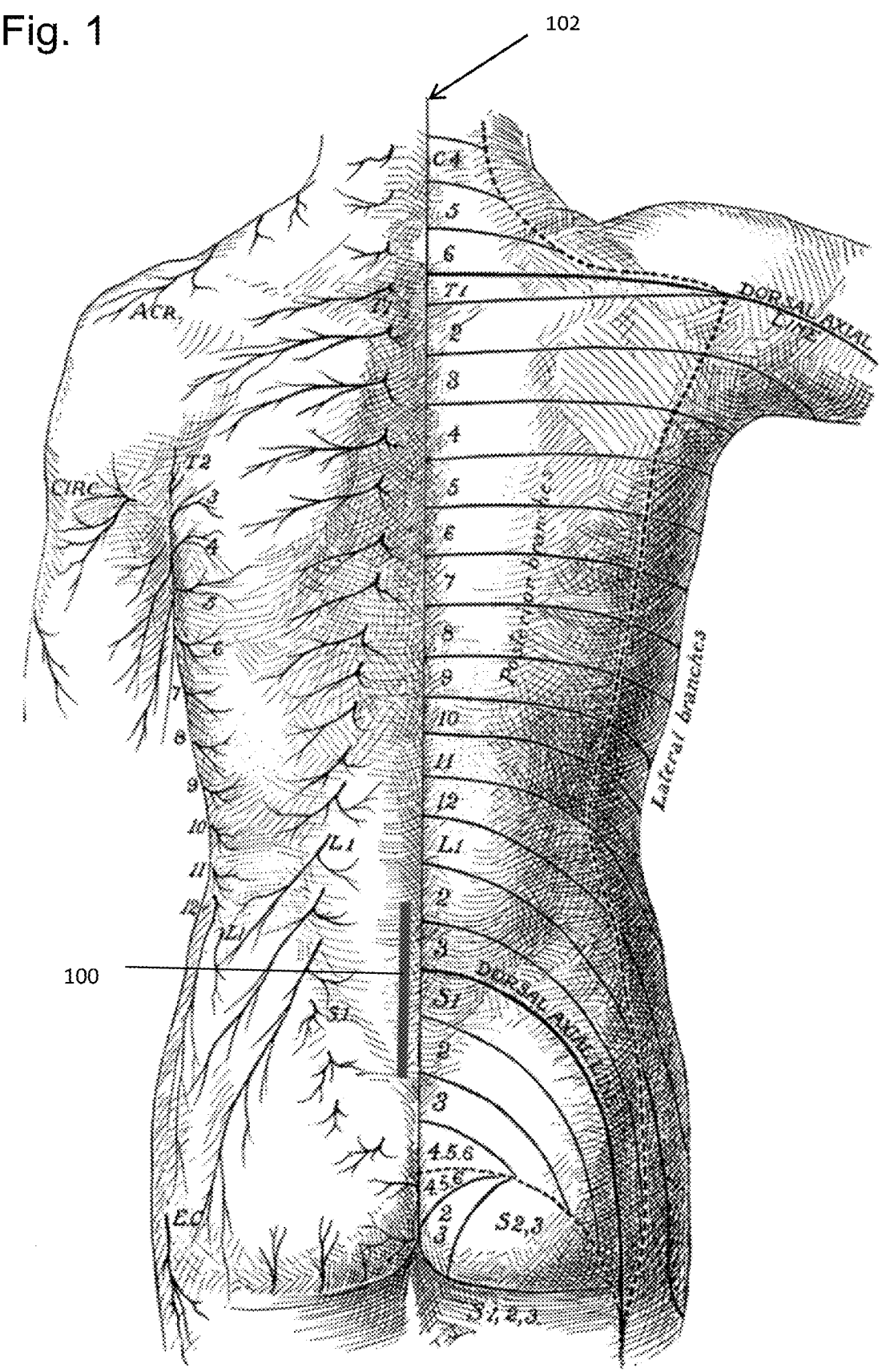
FIG. 1 is an illustration showing the posterior cutaneous nerves.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail; although it will be apparent to those skilled in the relevant art that some features that are not relevant to the present invention may not be shown for the sake of clarity.

As used here (claims, specification, and other definitions) the following terms have the following meaning:

Articles and phases such as, "the", "a", "an", "at least one", and "a first", "comprising", "having" and "including" here are not limited to mean only one, but rather are inclusive and open ended to also include, optionally, two or more of such elements and/or other elements. In terms of the meaning of words or terms or phrases herein, literal differences therein are not superfluous and have different meaning, and are not to be synonymous with words or terms or phrases in the same or other claims.

The term "means for" in a claim invokes 35 U.S.C. § 112(f), literally encompassing the recited function and corresponding structure and equivalents thereto. Its absence does not, unless there otherwise is insufficient structure recited for that claim element. Nothing herein or elsewhere restricts the doctrine of equivalents available to the patentee.

The term "and/or" is inclusive here, meaning "and" as well as "or". For example, "P and/or Q" encompasses, P, Q, and P with Q; and, such "P and/or Q" may include other elements as well.

The term "anesthetizing" as used herein has the meaning, a process for providing temporary loss of sensation, muscle control, and/or awareness.

The term "anterior" as used herein has the meaning, being situated nearest or toward the front of the body. With respect to the spine, the anterior is considered to be the side of the spine closest to the stomach or the throat.

The term "anteriorly" as used herein has the meaning, positioned in a location more anterior with respect to another object where the anterior refers to a position nearer to the front of a reference point.

The term "body portion" as used herein has the meaning, the main or principal part of an object. More specifically, it refers to the part of a vertebra implant that contacts the vertebral body of a neighboring vertebra.

The term "contact" as used herein has the meaning, of two objects the state or condition of physical touching. As used, contact requires at least one location where objects are directly or indirectly touching, with or without any other member(s) material in between.

The term "cranial-caudal orientation" as used herein has the meaning, in the direction along an axis running vertically toward and away from a (standing) patient's skull.

The term "cranial direction" as used herein has the meaning, in the direction toward the patient's head along the cranial-caudal axis.

The term "caudal direction" as used herein has the meaning, in the direction towards the patient's feet along the cranial-caudal axis.

The term "cryoanalgesia" (also known as cryoneurolysis) as used herein has the meaning is the reversible destruction of the signal carrying parts of a nerve. It is a small subset of treatments under the broad umbrella of cryotherapy.

The term "cryo-needle" as used herein has the meaning, a medical device having a slender, usually sharp pointed body and configured to cause freezing at the distal end, (which may include its tip, but also may be portions near to but proximal to the tip), upon activation.

The term "discectomy" as used herein has the meaning, a surgical removal of all or part of an intervertebral disc.

The term "dorsal ramus" as used herein has the meaning, the posterior division of a spinal nerve that forms the dorsal root of the nerve as it emerges from the spinal cord.

The term "Erector Spinae Plane Block" as used herein has the meaning, a paraspinal fascial plane block that involves injection of local anesthetic between the erector spinae muscle and the transverse process, thus blocking inhibiting the dorsal and/or ventral rami of the spinal nerve. Upon injection the local anesthetic spreads in a cranial and/or caudal direction inhibiting the dorsal and or ventral rami of neighboring spinal nerves along the spinal cord.

The term "facilitate" as used herein has the meaning, to aid or help accomplish an action or a process to make that action or process easier. The act of facilitation does not need to accomplish the action or process entirely on its own.

The term "front surface" as used herein has the meaning, an exterior surface which may or may not be the anterior most surface.

The term "hole" as used herein has the meaning, a hollow opening within a body, structure, or an object. It can be any shape.

The term "imageable" as used herein has the meaning, a device which is configured to allow for medical imaging of the device during use such as by computed tomography (CT), magnetic resonance (MRI), positron emission tomography (PET), fluoroscopy, and/or ultrasonography. As used herein the "imageable" device is configured to allow a user to visualize all or a portion of the device within the patient during a procedure.

The term "laminectomy" as used herein has the meaning, a surgical operation to remove the back of one or more vertebrae, usually to give access to the spinal cord or to relieve pressure on nerves.

The term "pain block" as used herein has the meaning, inhibition of one or more sensory nerves that relay pain signals to a target region of the patient's body.

The term "local anesthesia" as used herein has the meaning, a medication that causes reversible absence of pain sensation in a target area of the body. When it is used on specific nerve pathways, paralysis also can be achieved.

The term "sensory nerve" as used herein has the meaning, a nerve that carries sensory information toward the central nervous system (CNS).

The term "side" as used herein has the meaning, one of the faces on the surface of an object. An object can have multiple faces with a variety of orientations. For example, an object may have a front side, a bottom side, a back side, or a top side.

The term "spinal fusion" as used herein has the meaning, a neurosurgical or orthopedic surgical technique that joins two or more vertebrae. This procedure can be performed at any level in the spine and prevents any movement between the fused vertebrae. Spinal fusion may also be called spondylodesis or spondylosyndesis.

The term "spinal surgery" as used herein has the meaning, any surgical procedure including the patient's spinal cord.

The term "superficial" as used herein has the meaning, a directional term that indicated one structure is located more externally than another, or closer to the surface of the body.

The term "transverse" as used herein has the meaning, situated or extending across an object or an axis.

The term "vertebra" as used herein has the meaning, a bone or object that forms part of the spinal column. The vertebra could be composed of bone or it can be an implant formed from any variety of materials that would be useful to replace bone such as titanium, stainless steel, or other metallic or non-metallic compounds.

The term "withdrawal" as used herein has the meaning, the action of removing or taking away something for a particular location.

Until now, traditional cryotherapy treatments were invasive, and used large complicated machines. A new generation of cryo-needles has revolutionized the delivery of cryoanalgesia. One example is the iovera system by Myoscience.

With cryo-needle systems, doctors are able to deliver precise, controlled doses of cold temperature only to the targeted nerve through a handheld device. This needle-based procedure is safe, and does not damage or destroy the surrounding tissue.

These cryo-needle based treatments use the body's natural response to cold to treat peripheral nerves and immediately reduce pain—without the use of drugs. Treated nerves are temporarily stopped from sending pain signals for a period of time, followed by a restoration of function.

It is important to note that cryo-needle therapy, such as the ioverao therapy, does not treat the underlying cause of the pain. Timely remediation is necessary to address and treat the cause of pain.

Cryo-needle therapies, such as the iovera treatment, work by applying targeted cold to a peripheral nerve. A precise cold zone is formed under the skin—cold enough to immediately prevent the nerve from sending pain signals without causing damage to surrounding structures. The effect on the nerve is temporary, providing pain relief until the nerve regenerates and function is restored.

Cryo-needle therapies, such as the ioverao treatment, generally do not include injection of any substance—drugs, opioids or narcotics. The effect of this treatment is immediate and can last weeks to several months depending on the multiple factors, including the patients anatomy and pain tolerance. In one study, majority of the patients suffering from osteoarthritis of the knee have experienced pain and symptom relief beyond 150 days." See also, Radnovich, R. et al. "Cryoneurolysis to treat the pain and symptoms of knee osteoarthritis: a mulitcenter, randomized, double-blind, sham-controlled trial." Osteoarthritis and Cartilage (2017) p1-10. (incorporated herein by reference) Cryo-needle therapies, such as the lovera technology, use FDA approved devices that have needles with ends that create ice balls, allowing targeted nerves to be stunned, and completely reversible weeks to months later. This technology has allowed tremendous pain control for orthopedic procedures such as total knee and total hip replacement. Freezing the sensory skin nerves of the anterior thigh for total knee replacement and the lateral thigh for hip replacement has resulted in significant drops in opioid need and postoperative pain scores. Similar results are available for sensory freezing the posterior cutaneous nerves of the spine. Freezing cutaneous nerves alone may not provide sufficient pain relief. We have supplemented the cryoanalgesia treatment with a nerve block called an Erector Spinae Block. Erector spinae blocks are generally placed by physicians, for example anesthesiologists, using ultrasound. Erector spinae blocks may also be placed by surgeons using guided navigation surgery software. Using cryo-needle technology for previously untried lumbar fusion spine procedures provides surprising success. Other possible applications include anesthesia pain blocks for chronic pain, thus avoiding more invasive epidural steroid injections. Routine lumbar discectomy and laminectomy patients could receive cryo-needle treatment at the end of surgeries. More complex cervical and thoracic spine applications may also be possible.

Sensory nerves that are targeted for pain relief may innervate anterior, posterior, and/or lateral parts of the body. In certain embodiments the current disclosure provides methods of anesthetizing a patient undergoing surgical procedures at or in anterior, posterior, and/or lateral parts of the body.

The lateral region of the body includes lateral portions of the thorax as well as extremities, hips, knees, arms, elbows, shoulders, hands, feet, and legs.

The anterior region of the body which may be anesthetized using the provided methods includes for example: skin, muscle, nerves, bones, chest wall, breast, esophagus, trachea, lungs, pleura, diaphragm ,mediastinum, heart, pericardium, great vessels with and without pump oxygenator, anterior cervical spine, anterior thoracic spine, anterior lumbar spine, upper anterior abdominal wall including hernias (lumbar, ventral, umbilical, incisional, diaphragmatic, omphalocele), anterior major abdominal blood vessels, spleen, liver, pancreas, liver, anterior lower abdomen wall (hernias), kidney uterus, bladder, adrenal glands, prostate, vagina, and/or anterior pelvis. Surgical procedures which may be performed in conjunction with the anterior region of the body in accordance with the present disclosure include, for example: thoracoscopy, thoracotomy, transplant, anterior intraperitoneal procedures such as spleen, liver, pancreas, liver transplant, and/or gastric bypass, abdominoperineal resection, hysterectomy, pelvic exenteration, nephrectomy, adrenalectomy, renal transplant, prostatectomy, and/or vaginal procedures.

The posterior region of the body which may be anesthetized using the provided methods includes, for example: cervical spine, thoracic spine, lumbar spine sacral spine, extensive complex spine and spinal cord instrumentation cervical spine to sacral spine FIG. 1 is an illustration showing the posterior cutaneous nerves. In certain aspects a target region 100 may be identified for cryoneurolysis. For example in the illustrated embodiment the target region 100 spans a generally linear region lateral to midline 102 and extending along the spinal column from L2 to S2. The illustrated target region extends generally from L2 to S3. It is to be understood that a target region for use with any embodiment disclosed herein can extend over, and thus target nerves emerging from, any number of vertebral segments including C1 through C7, T1 through T12, L1 through L3, as well as the sacrum and coccyx. It is also within the scope of the disclosure that multiple target regions may be treated in a single procedure.

Figure 2:
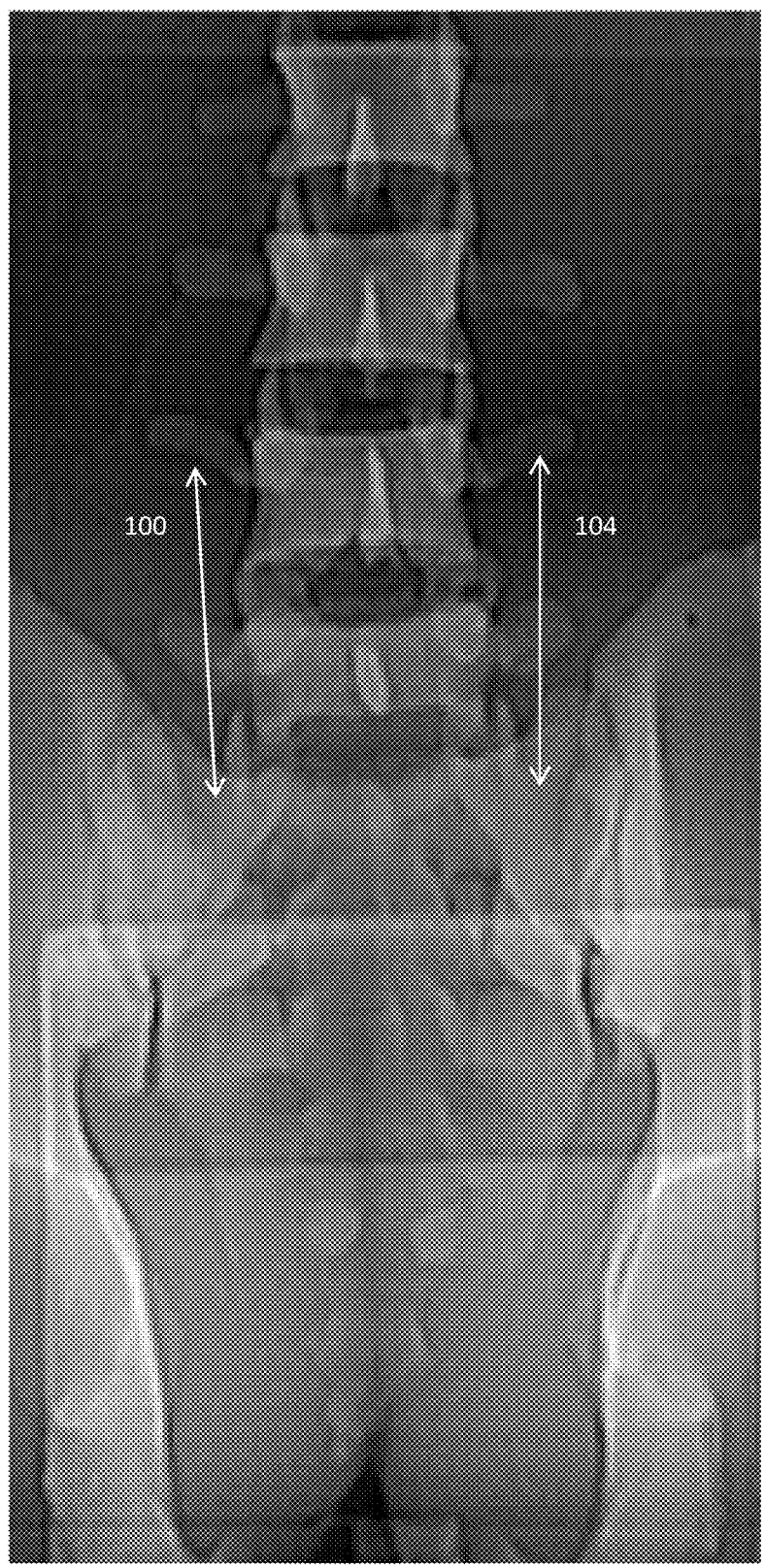
FIG. 2 is a fluoroscopic image of a portion of a patient's spinal column.

FIG. 2 is a fluoroscopic image of a portion of a patient's spinal column. In the illustrated embodiment the patient is being prepped for L4-L5 lumbar fusion. In the illustrated embodiment the top of L4 and bottom of L5 vertebral bodies are identified, the transverse process of L4 and L5 are identified, a first target region 100 is drawn at the mid distance width of the transverse process. In the illustrated embodiment a second target region 104 is identified opposing the first target region 100. Cryoneurolysis is done along the target regions 100 and/or 104 from the top of L4 to the bottom of L5, transverse process mid distance from the vertebral body.

Figure 3:
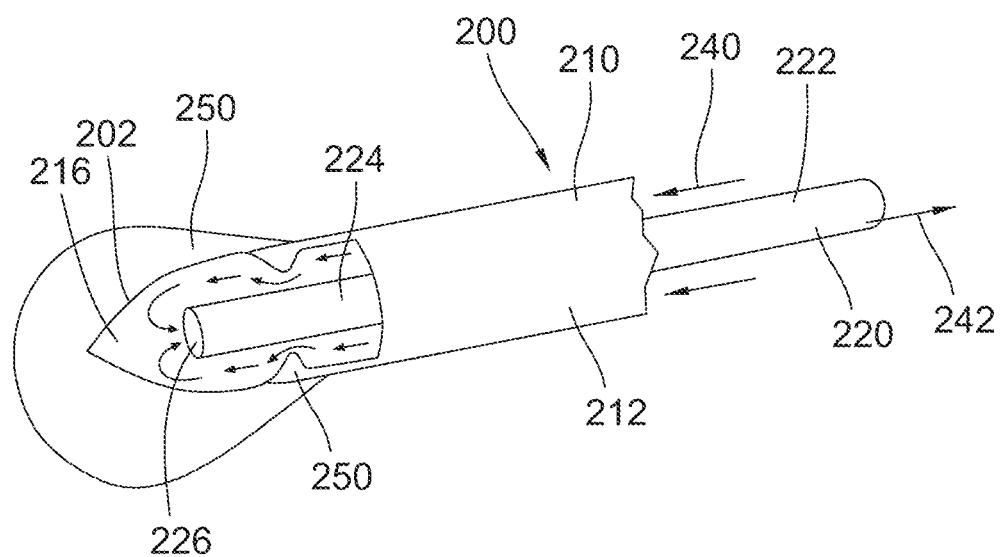
FIG. 3 illustrates the distal portion of an example of a cryo-needle for use with the presently disclosed methods.

FIG. 3 illustrates the distal portion of one embodiment of a cryo-needle for use with the presently disclosed methods. Briefly, cryo-needle 200 comprises body wall 210 having outer surface 212 and inner surface 214, inner surface 214 defining inner lumen 216 defining a first fluid flow path 240. Needle end 202 is positioned near the distal most portion of the needle. Cannula 220 is disposed within inner lumen 216. Cannula 220 comprises cannula wall 222 having an outer cannula surface 224 and inner cannula surface 226. Inner cannula surface 226 defining a second fluid flow path 242. In the illustrated embodiment a cooling fluid and/or gas travels distally through the first fluid flow path to the needle end. The cooling fluid and/or gas causes an ice ball 250 to form at the needle end, and returns through the second fluid flow path 242. In certain embodiments needle end 202 may include a Joule-Thomson annulus 250.

Figure 4:
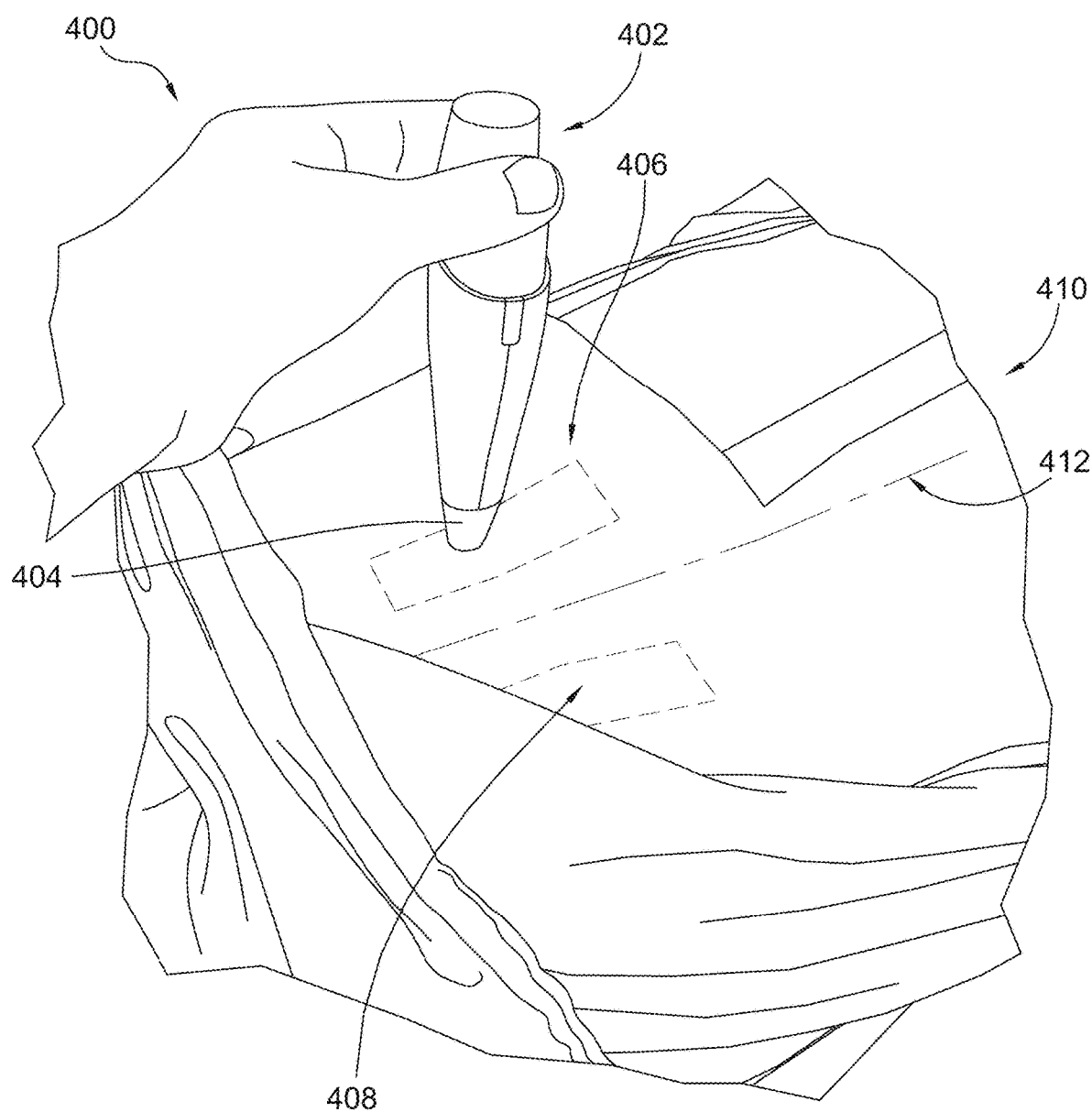
FIG. 4 illustrates one embodiment of a method for anesthetizing a human patient.

FIG. 4 depicts one embodiment of a method of anesthetizing a patient as disclosed herein. In the illustrated embodiment a user 400, for example a physician positions a cryo-needle device 402, having one or more cryo-needle ends as discussed herein positioned at or near a distal portion 404 of the cryo-needle device, at a first target region 406 on patient 410. In the illustrated embodiment the first target region opposes a second target region 408 over midline 412. Midline 412 is superficial to the patients' spine such that target regions 406 and 408 are both lateral to the midline along the patients' spine. In certain embodiments a target region comprises soft tissue superficial to one or more target spinal nerves. Thus in certain embodiments a target region is selected to target underlying spinal nerves. In the illustrated embodiment one or more cryo-needle ends are inserted into the first target region. In accordance with the present disclosure the needle ends are cooled to cause cooling of surrounding patient tissue, thus inhibiting one or more of the target spinal nerves in the surrounding tissue. In certain embodiments, multiple insertion and cooling cycles are performed within a given target region. In accordance with some forms of practicing the disclosed method, a second target region opposing the first target region may also be treated in a similar fashion, thus bilaterally anesthetizing a region of the patients' spine.

Figure 5:
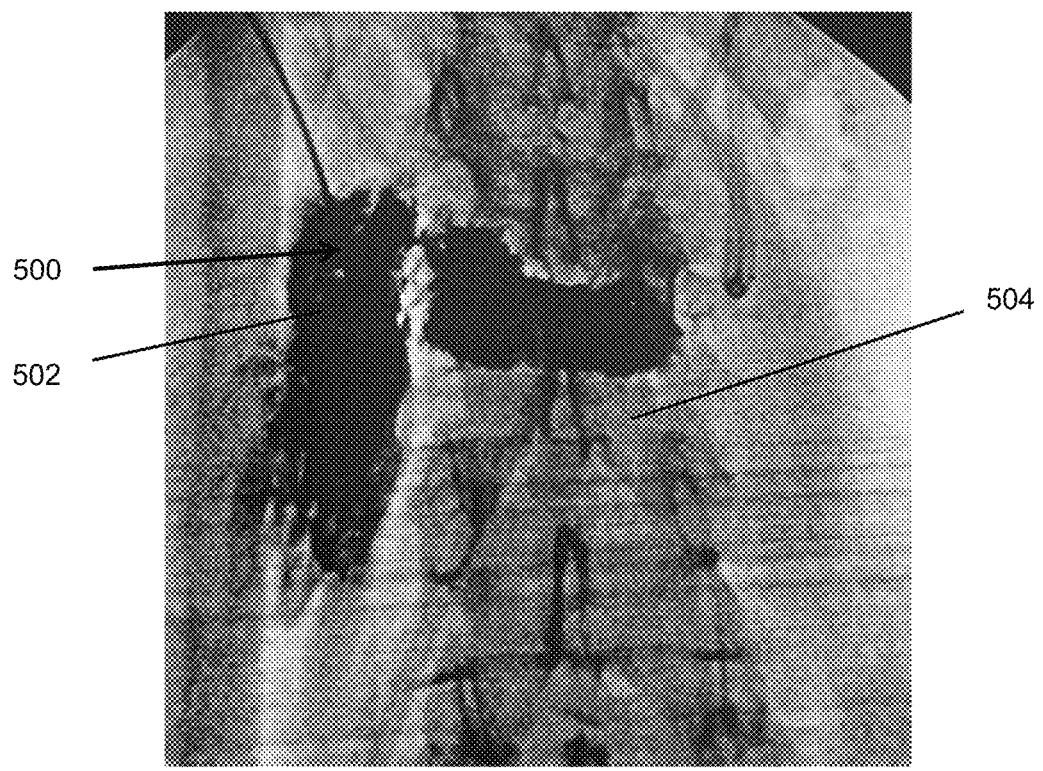
FIG. 5 is a fluoroscopic image showing migration of anesthetic and contrast agent injected during an erector spinae block procedure.

FIG. 5 is a fluoroscopic image of a portion of a patient's spinal column 504. In the illustrated embodiment, migration of anesthetic and contrast agent 502 injected during an erector spinae block procedure is evident. The image clearly shows anesthetic migrated in both a cranial and caudal direction from the locus of injection 500, allowing for analgesic effect on spinal nerves pass through the affected area.

In certain embodiments the present disclosure provides a method for anesthetizing a human patient undergoing surgery, and/or pain block procedures, the method comprising: sterilizing the patient's skin including a target region, the target region including a surgical site including the patient's spine; inserting at least one cryo-needle into a first tissue region, the cryo-needle having a distal end configured to cool surrounding patient tissue, the first tissue region comprising soft tissue superficial to the one or more vertebra and on a first lateral side of the patients spine; cooling the distal end of the cryo-needle to cause cooling of surrounding patient tissue thus inhibiting one or more sensory nerves in the surrounding patient tissue; thereafter, performing spinal surgery on the patient's spine at the surgical site; and, thereafter, performing an erector spinae plane block to further inhibit nerves post-operatively in the target region.

In some forms the surgery comprises one or more of an anterior, posterior, lateral, and/or spinal surgery, wherein the area surgically treated is innervated by a spinal nerve. In some forms the spinal surgery comprises at least one of: a spinal fusion, a discectomy, a laminectomy, and/or a pain block. In certain embodiments, the one or more inhibited nerves includes nerves of the dorsal ramus.

In certain embodiments, both the erector spinae needle and cryoneurolysis needles may be insulated, thus allowing electrical stimulation and evaluation of motor function.

In certain embodiments, the erector spinae plane block is performed with a local anesthesia. In some forms the local anesthesia is delivered using an imageable needle.

In certain embodiments the erector spinae plane block is performed using an elongate cryo-needle. In some forms the elongate cryo-needle is imageable.

In accordance some forms of practicing the disclosed methods, an imageable cryo-needle is used, such that the erector spinae block and/or the cryo-needle are placed using guidance from a medical imaging device.

In certain embodiments the cryo-needle comprises two or more needle ends configured to cool surrounding patient tissue. In some forms the two or more needle ends are configured in a generally linear array.

In certain embodiments the above method further comprises inserting at least one cryo-needle into a second patient tissue region, the cryo-needle having a distal end configured to cool surrounding patient tissue, the second patient tissue region comprising soft tissue superficial to the one or more vertebra and on a second lateral side of the patients spine opposing said first tissue region.

In certain embodiments the inserting and cooling steps are repeated along a portion of the patients spinal column. In some forms the inserting and cooling steps are repeated in such a way so that progressing in a cranial or caudal direction each subsequent target region is laterally offset from the prior target region.

In certain embodiments the present disclosure provides a method for anesthetizing a patient, the method comprising: inserting at least one cryo-needle into a first tissue region, the cryo-needle having a distal end configured to cool surrounding patient tissue, the first tissue region comprising soft tissue superficial to one or more vertebra and on a first lateral side of the patients spine; cooling the distal end of the cryo-needle to cause cooling of surrounding patient tissue at the first tissue region thus inhibiting one or more sensory nerves in the surrounding tissue; inserting at least one cryo-needle into a second tissue region, the cryo-needle having a distal end configured to cool surrounding patient tissue, the second tissue region comprising soft tissue superficial to one or more vertebra and on the first lateral side of the patient's spine; and cooling the distal end of the cryo-needle to cause cooling of surrounding patient tissue at the second tissue region thus inhibiting one or more sensory nerves in the surrounding tissue.

In certain embodiments the above method also comprises inserting at least one cryo-needle into a third tissue region, the cryo-needle having a distal end configured to cool surrounding patient tissue, the third tissue region comprising soft tissue superficial to one or more vertebra and on the first lateral side of the patient's spine; and cooling the distal end of the cryo-needle to cause cooling of surrounding patient tissue at the third tissue region thus inhibiting one or more nerves in the surrounding tissue.

In certain embodiments the cryo-needle comprises two or more needle ends configured to cool surrounding patient tissue. In some forms the two or more needle ends are configured in a generally linear array.

In certain embodiments the inserting and cooling steps are repeated along a portion of the patient's spinal column. In some forms the inserting and cooling steps are repeated in such a way so that progressing in a cranial or caudal direction each subsequent tissue region is laterally offset from the prior target region.

In certain embodiments the inserting and cooling steps are repeated on the second lateral side of the patient's spine.

In certain embodiments the method further comprising performing spinal surgery on the patient's spine. In some forms the spinal surgery comprises at least one of: a spinal fusion, a discectomy, and/or a laminectomy.

In certain embodiments the one or more inhibited nerves includes nerves of the dorsal ramus.

Alternatively, or in combination with the above guided surgical navigation software has developed and evolved over the past two decades. For example, the Stealth surgical navigation system by Medtronic. Today, surgeons (e.g. neurosurgeon or orthopedic spine surgeon) rely on proper software for complex spine procedures. Evolution of surgical practice lead to innovations like CT/MRI guided fusions, passive markers, touch screen displays and laser surface registration. Postoperative multimodal pain pathways have been marginal at best for controlling severe pain associated with these complex spine procedures. Regional anesthesia pain blocks have not been commonly practiced with spine surgery for multiple reasons. For example, guided navigation requires sensory monitoring of spinal cord signals throughout the procedure. Local anesthetics would, or may, prevent or impede sensory monitoring. Thus, preoperative pain blocks using conventional local anesthetics before surgery is not normally possible. In addition, reducing postoperative pain with local anesthetic pain blocks may mask inadvertent surgical epidural hematoma.

The current inventor has confirmed the efficacy of effective pain control allowing same day ambulation after complex spine fusion using Erector Spinae Plane Block (ESPB) in combination with cryoanalgesia. After cryo-needle treatment along a target region of the spine, ESPB catheters were placed by ultrasound above the anticipated surgical site before surgery. The catheters were dosed with local anesthetic at the end of surgery.

Placing ESPB catheters may be difficult and reproducibility requires experienced anesthesia. We have performed surgeon intraoperative single injection ESPB in the surgical field using generic regional anesthesia block needles. The ESPB block was aided using guided navigation software and a guided pointer to safely facilitate placement on the transverse process for appropriate block. The following is needed for repeatable, safe, precision placement for intraoperative surgeon placed ESPB:

1. A guided navigation surgery software compatible block needle with attached tubing for surgeon intraoperative direct placement of local anesthetic for an ESPB. Guided navigation technology in an actual block needle will easily allow precise depth and location placement.

2. Some may elect not to use a "guided navigation surgery software compatible block needle" to perform an ESPB. Alternatively, a guided navigation surgery software compatible sheath or similar device would allow guided entry for the following: regional anesthesia block needle to be used through the guided navigation software compatible sheath device for ESPB, and/or any available cryoneurolysis needle to be placed through the sheath device precisely into a surgical site.

3. A guided navigation surgery software compatible cryoneurolysis needle. Current cryoneurolysis needle techniques use anatomic landmarks, ultrasound, or fluoroscopy for guidance to target areas. A guided navigation surgery software compatible cryoneurolysis needle would not require a navigation sheath for skin entry and could be used directly on target surgical area.

4. Use of a non-guided navigation surgery software compatible ESPB needle with tubing, identical to the guided navigation surgery software compatible ESPB needle, to allow a surgeon to perform an intraoperative single injection ESPB guided by fluoroscopy, for routine spine procedures. Physicians are comfortable with similar designs.

The invention may include any one or more articles or devices made by any of the claimed methods and/or may by different methods but with a claimed composition.

The language used in the claims and the written description and in the above definitions is to only have its plain and ordinary meaning, except for terms explicitly defined above. Such plain and ordinary meaning is defined here as inclusive of all consistent dictionary definitions from the most recently published (on the filing date of this document) general purpose Webster's dictionaries and Random House dictionaries.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A method for anesthetizing a human patient undergoing surgery and surgery pain block procedures, the method comprising the acts of:
   sterilizing the patient's skin including a target region, the target region including a site including a portion of the patient's spine associated with one or more target spinal nerves which innervate a surgical site for the surgery;
   inserting at least one cryo-needle into a first tissue region, the cryo-needle having a distal end configured to cool surrounding patient tissue, the first tissue region comprising soft tissue superficial to the target spinal nerves and on a first lateral side of the patients spine;

cooling the distal end of the cryo-needle to cause cooling of surrounding patient tissue thus inhibiting one or more of the target spinal nerves in the surrounding patient tissue;

thereafter, performing surgery on the patient at the surgical site; and, thereafter, performing an erector spinae plane block to further inhibit nerves post-operatively in the target region.

2. The method of claim 1, wherein the surgery comprises one or more of an anterior, posterior, lateral, and/or spinal surgery.

3. The method of claim 2, wherein the spinal surgery comprises at least one of: a spinal fusion, a discectomy, a laminectomy.

4. The method of claim 1, wherein the one or more inhibited nerves includes nerves of the dorsal ramus.

5. The method of claim 1, wherein the erector spinae plane block is performed with a local anesthesia.

6. The method of claim 5, wherein the local anesthesia is delivered using an imeagable needle.

7. The method of claim 5, wherein the erector spinae plane block is performed using an elongate cryo-needle.

8. The method of claim 7, wherein the elongate cryoneedle is imageable.

9. The method of claim 5, wherein the cryo-needle comprises two or more needle ends configured to cool surrounding patient tissue.

10. The method of claim 9, wherein the two or more needle ends are configured in a generally linear array.

11. The method of claim 1, further comprising inserting at least one cryo-needle into a second patient tissue region on the same patient, the cryo-needle having a distal end configured to cool surrounding patient tissue, the second patient tissue region comprising soft tissue superficial to one or more vertebra and on a second lateral side of the patients spine opposing said first tissue region.

12. The method of claim 11, wherein said inserting and said cooling steps are repeated along a portion of the patients spinal column.

13. The method of claim 12, wherein said inserting and said cooling acts are repeated in such a way so that progressing in a cranial or caudal direction each subsequent target region is laterally offset from the prior target region.

* * * * *